United States Patent
Liao et al.

(10) Patent No.: US 10,483,881 B2
(45) Date of Patent: Nov. 19, 2019

(54) SYSTEMS AND METHODS FOR MOTOR TORQUE COMPENSATION

(71) Applicant: INTUITIVE SURGICAL OPERATIONS, INC., Sunnyvale, CA (US)

(72) Inventors: Hsien-Hsin Liao, Sunnyvale, CA (US); Niels Smaby, Palo Alto, CA (US); Gregory W. Dachs, II, San Mateo, CA (US); Pushkar Hingwe, Los Altos, CA (US); Amir Chaghajerdi, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 445 days.

(21) Appl. No.: 15/118,264

(22) PCT Filed: Feb. 17, 2015

(86) PCT No.: PCT/US2015/016093
§ 371 (c)(1),
(2) Date: Aug. 11, 2016

(87) PCT Pub. No.: WO2015/126803
PCT Pub. Date: Aug. 27, 2015

(65) Prior Publication Data
US 2017/0179857 A1 Jun. 22, 2017

Related U.S. Application Data

(60) Provisional application No. 61/954,451, filed on Mar. 17, 2014, provisional application No. 61/941,854, filed on Feb. 19, 2014.

(51) Int. Cl.
*A61B 34/30* (2016.01)
*A61B 34/37* (2016.01)
(Continued)

(52) U.S. Cl.
CPC ............... *H02P 6/10* (2013.01); *A61B 17/00* (2013.01); *A61B 34/35* (2016.02); *A61B 90/03* (2016.02);
(Continued)

(58) Field of Classification Search
CPC ............. H02P 23/14; H02P 6/15; H02P 29/64
See application file for complete search history.

(56) References Cited

U.S. PATENT DOCUMENTS

2004/0155547 A1* 8/2004 Islam ..................... H02K 1/278
310/156.43
2008/0075439 A1 3/2008 Huang
(Continued)

FOREIGN PATENT DOCUMENTS

KR 20040063524 A 7/2004

OTHER PUBLICATIONS

International Search Report and Written Opinion for Application No. PCT/US15/16093, dated May 27, 2015, 12 pages.
(Continued)

*Primary Examiner* — Bickey Dhakal
*Assistant Examiner* — Charles S Laughlin
(74) *Attorney, Agent, or Firm* — Haynes and Boone, LLP

(57) ABSTRACT

A method for torque compensation of a motor associated with a medical instrument includes determining a torque profile for a motor, the torque profile defining torque output as a function of rotor angle and during operation of the motor, compensating for deviations in the torque profile by adjusting an input signal to the motor, the compensating being based on the torque profile and rotor position.

20 Claims, 10 Drawing Sheets

(51) Int. Cl.
| | |
|---|---|
| *H02P 6/10* | (2006.01) |
| *H02P 6/08* | (2016.01) |
| *H02P 23/04* | (2006.01) |
| *H02P 23/00* | (2016.01) |
| *A61B 34/35* | (2016.01) |
| *A61B 90/00* | (2016.01) |
| *A61B 17/00* | (2006.01) |
| *H02P 6/14* | (2016.01) |

(52) U.S. Cl.
CPC .......... *H02P 6/08* (2013.01); *H02P 6/14* (2013.01); *H02P 23/0031* (2013.01); *H02P 23/04* (2013.01); *A61B 2017/00464* (2013.01); *A61B 2090/031* (2016.02); *A61B 2090/066* (2016.02); *A61B 2560/0223* (2013.01)

(56) References Cited

U.S. PATENT DOCUMENTS

| | | | |
|---|---|---|---|
| 2010/0204713 A1* | 8/2010 | Ruiz Morales | B25J 9/041 606/130 |
| 2012/0274248 A1 | 11/2012 | Fricker | |
| 2013/0119900 A1 | 5/2013 | Xiang et al. | |
| 2014/0253002 A1* | 9/2014 | Mikail | H02P 6/10 318/400.15 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEMS AND METHODS FOR MOTOR TORQUE COMPENSATION

RELATED APPLICATIONS

This application is the U.S. national phase of international application no. PCT/US2015/016093 (filed Feb. 17, 2015), which designated the United States and claimed right of priority to U.S. provisional patent applications no. 61/954,451 (filed Mar. 17, 2014) and 61/941,854 (filed Feb. 19, 2014), all of which are incorporated herein by reference.

FIELD

The present disclosure is directed to systems and methods for motor torque compensation, and more particularly to systems and methods for efficiently compensating for torque output variations for specific motors.

BACKGROUND

Electric motors are commonly used in a variety of applications. Such motors are electric machines that generate torque (or force, in the case of a linear motor) when supplied with an electric current. One type of electric motor is a DC brushless motor. When paired with a position sensor in a feedback loop, a DC brushless motor can provide accurate position control.

Electric motors may be used in a variety of applications. For example, teleoperative surgery involves the use of manipulator arms that move a medical instrument in a variety of spaces. Specifically, a brushless motor may be used to change the rotation, pitch, yaw, or position of a medical instrument. The brushless motor allows the operator of the instrument to put the device in a specific position based on putting the motor corresponding to each type of movement in a specific position.

Generally, there exists a fixed, nominal mapping between the current supplied to the motor, and the torque it produces. In reality, this mapping from the input current to the output torque of a brushless motor is generally not uniform over one rotor revolution. Specifically, at different rotation angles, the motor may produce a different torque output with the same input current. This is often referred to as a torque ripple. Torque ripples can affect the performance of the motor, and thus it is desirable to minimize or eliminate torque ripples.

SUMMARY

The embodiments of the invention are summarized by the claims that follow below.

In one embodiment, a method for torque compensation of a motor associated with a medical instrument includes determining a torque profile for a motor, the torque profile defining torque output as a function of rotor angle and during operation of the motor, compensating for deviations in the torque profile by adjusting an input signal to the motor, the compensating being based on the torque profile and rotor position.

In another embodiment, a motor system for driving an instrument of a teleoperative system comprises a brushless motor and a control system comprising a processor and a memory. The memory includes machine readable instructions that cause the system to store a compensation profile for controlling an input signal to the motor, the compensation profile defining adjustments to the input signal as a function of a rotor angle of the motor, and apply the compensation profile during operation of the motor.

In another embodiment, a teleoperative medical device includes a manipulator arm, a medical instrument detachably connected to the arm, a number of motors connected to the arm, each motor to move the instrument in a different manner, and a control system comprising a processor and a memory. The memory includes machine readable instructions that when executed by the processor, cause the system to store a separate compensation profile for each of the motors, the compensation profiles controlling an input signal to a respective motor, the compensation profiles defining adjustments to the input signals of respective motors as a function of a rotor angle of the motors, the compensation profiles being based on respective torque profiles associated with the motors, and apply the compensation profiles during operation of the motors.

In another embodiment, a method for compensating for torque ripples includes, during a calibration operation, determining how an amplitude of a torque ripple at a harmonic frequency varies with varying current input to a motor, storing a sensitivity profile for the motor at the harmonic frequency, the sensitivity profile defining how the amplitude of the torque ripple at the harmonic varies with varying current input, and during operation of the motor, using the sensitivity profile to compensate for the torque harmonic at the harmonic frequency.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
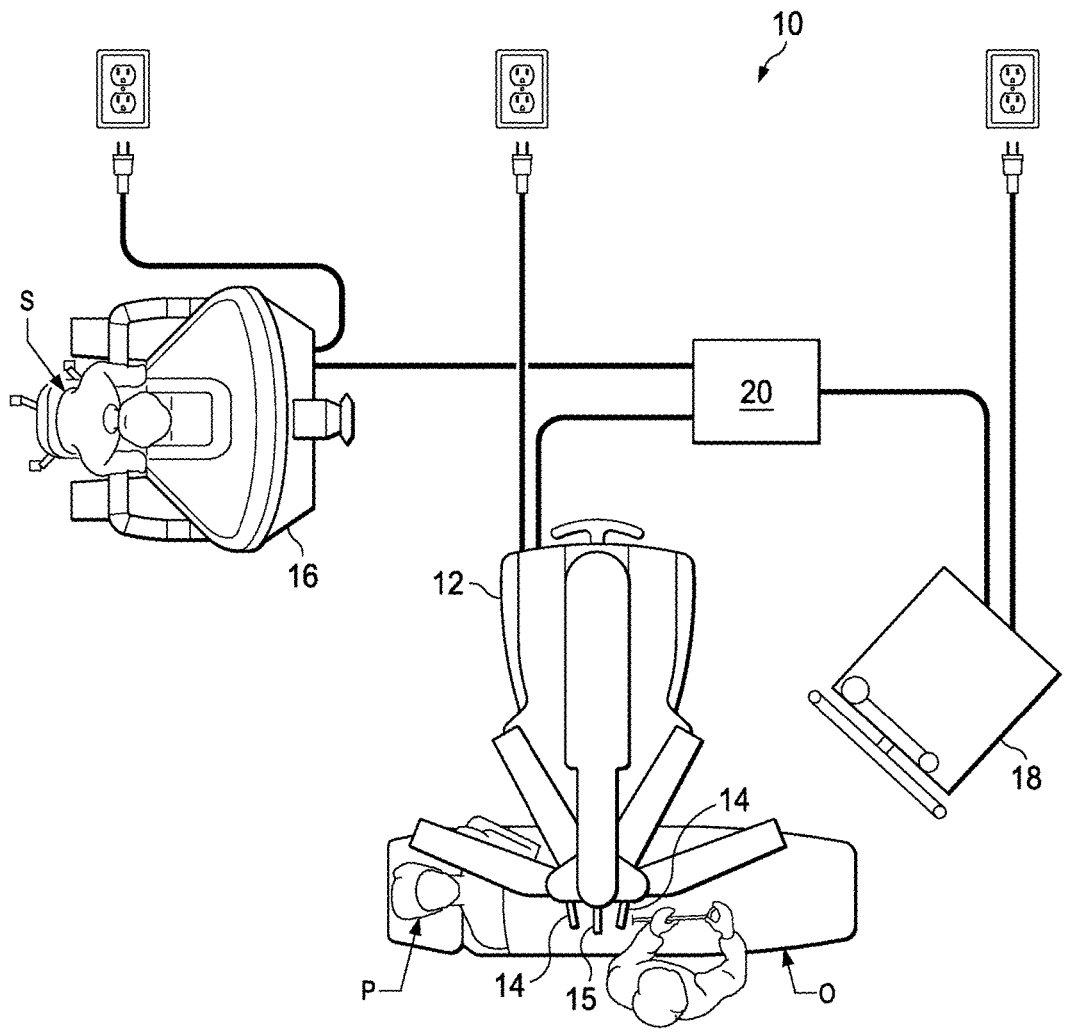
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 is operably coupled to the teleoperational assembly 12. An operator input system 16 allows a surgeon or other type of clinician S to view images of or representing the surgical site and to control the operation of the medical instrument system 14.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by an endoscope 15, such as a stereoscopic endoscope, which can be manipulated by the teleoperational assembly 12 to orient the endoscope 15. An electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system.

The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
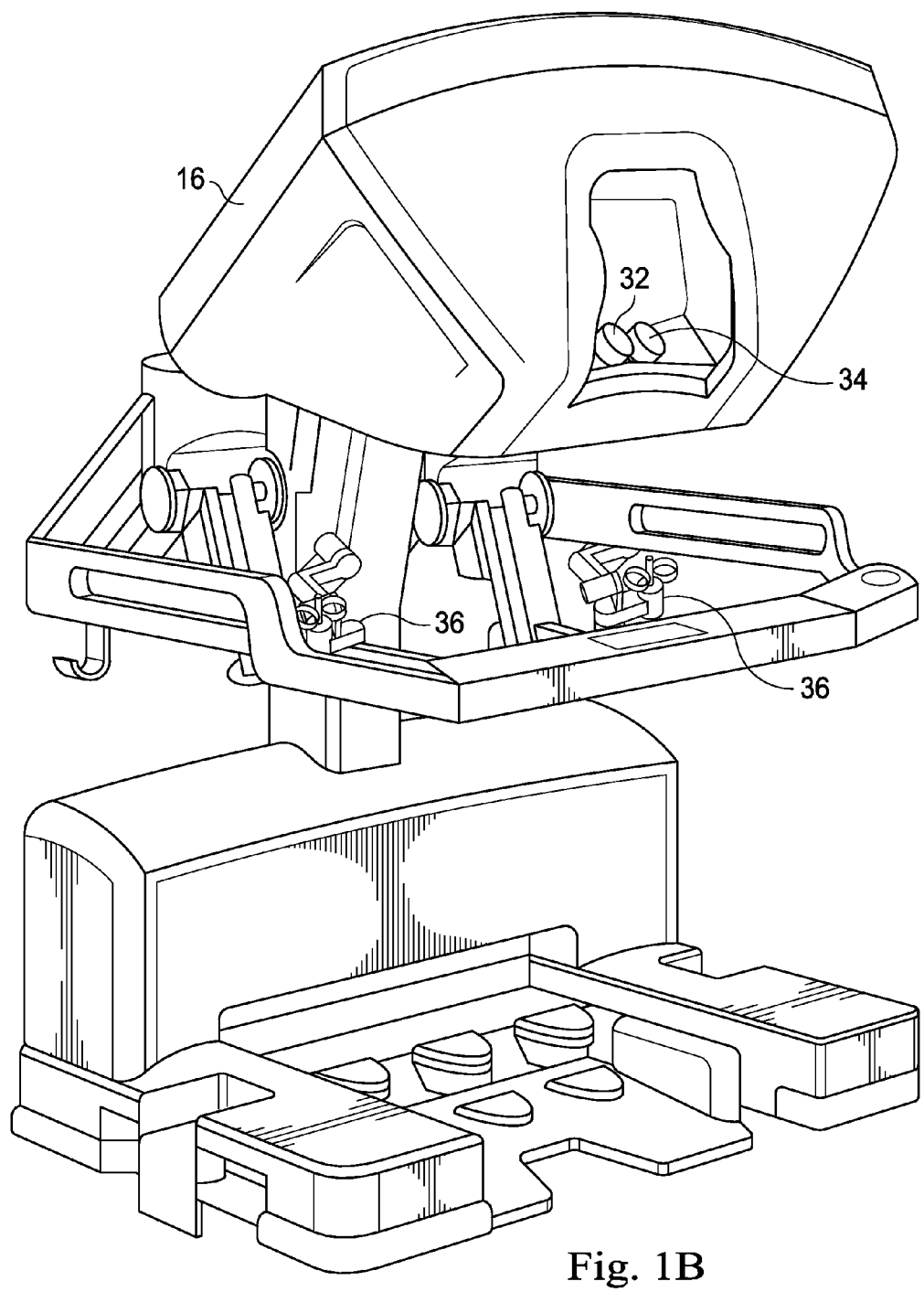
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more tools. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
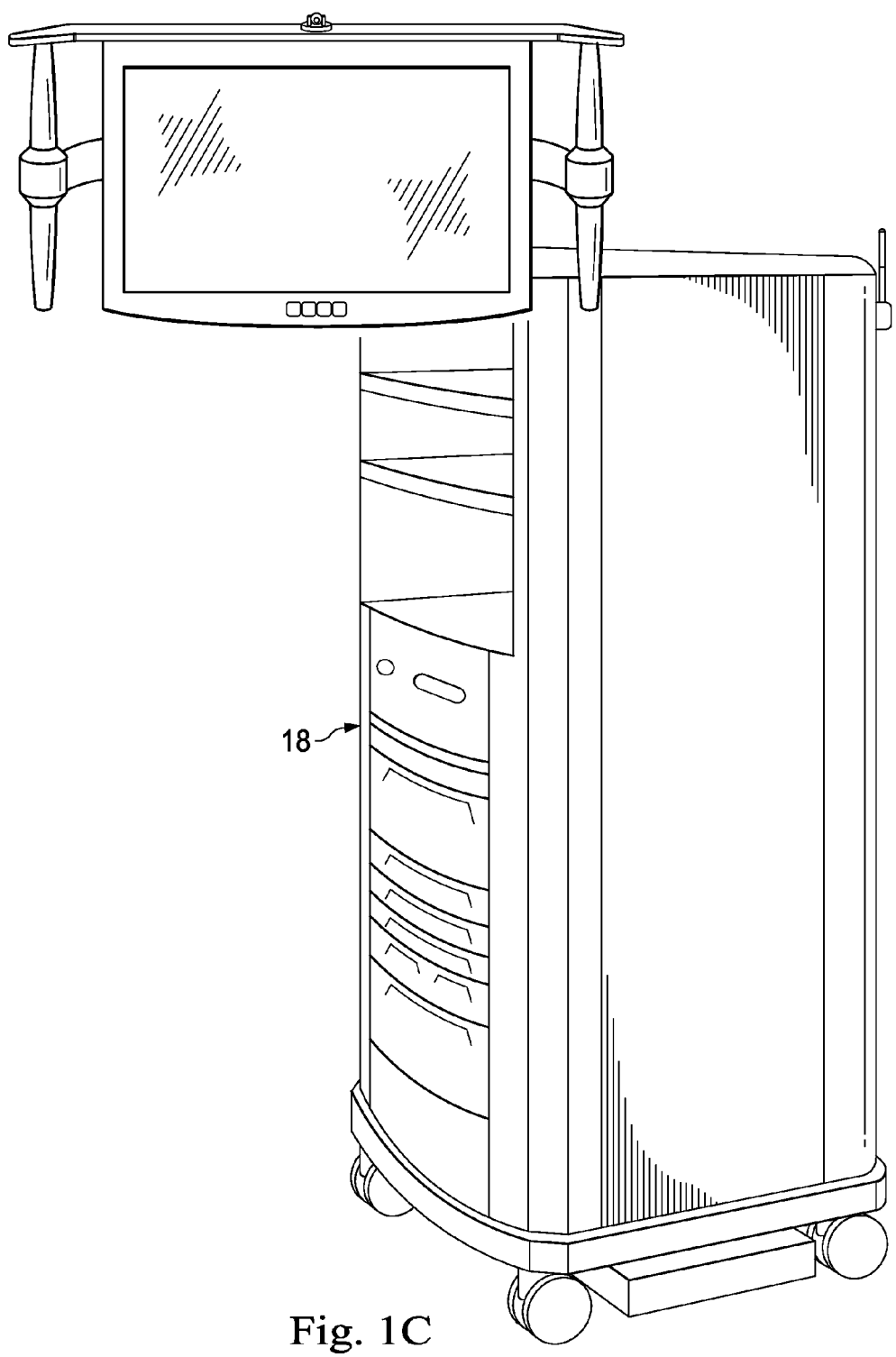
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
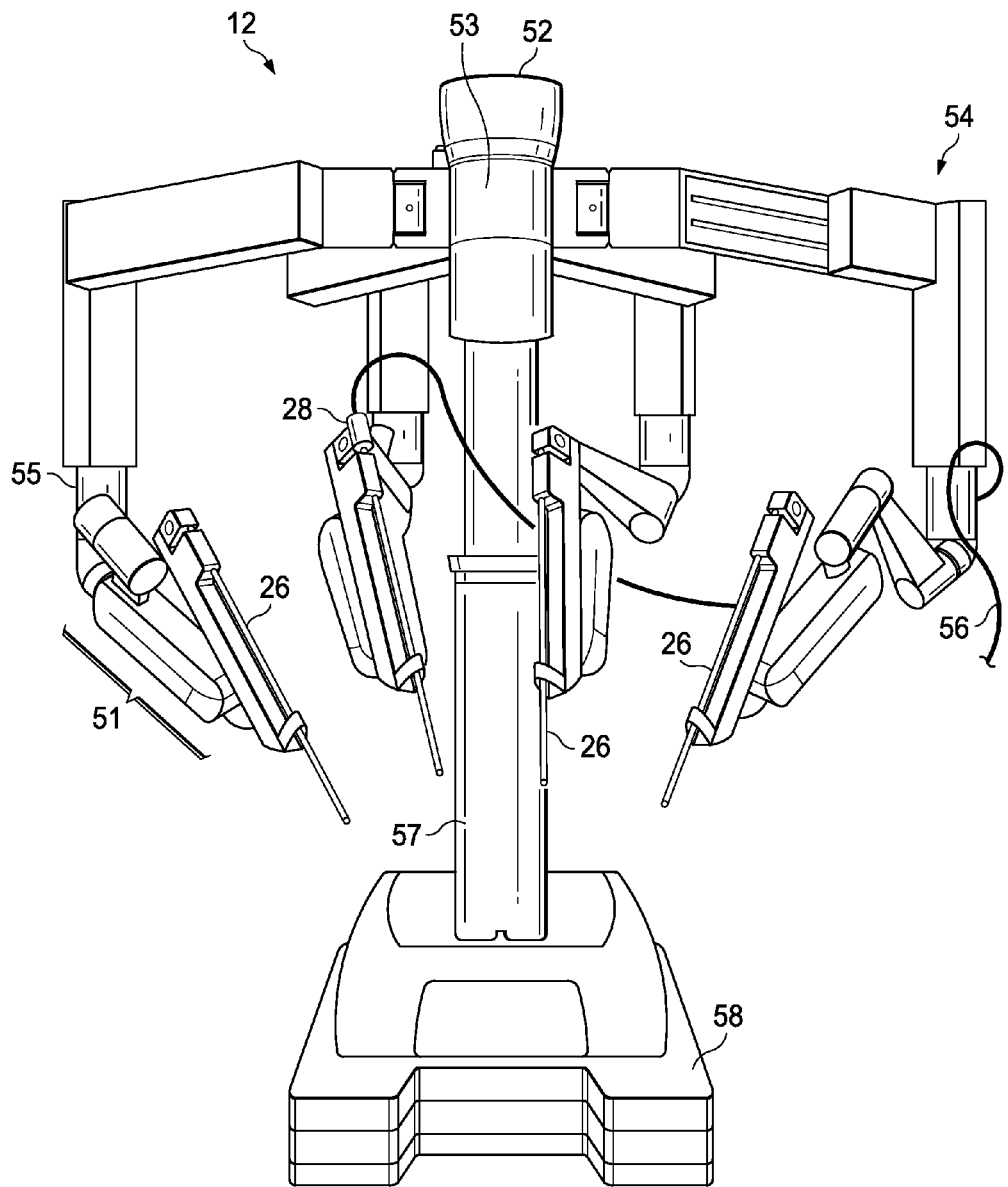
FIG. 1D is a perspective view of a patient side cart, according to one example of principles described herein.

FIG. 1D is a perspective view of a teleoperational assembly 12 which may be referred to as a patient side cart. The patient side cart 12 shown provides for the manipulation of three surgical tools 26 and an imaging device 28, such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

The patient side cart 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon begins operation with the teleoperative components.

Figure 2A:
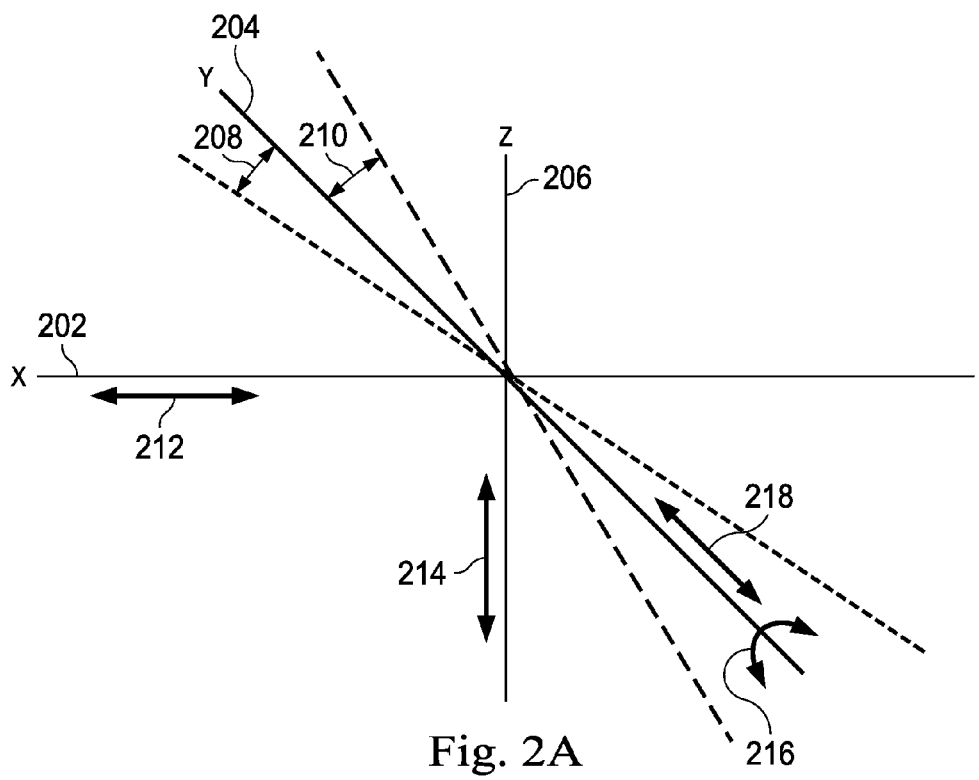
FIG. 2A is a diagram showing possible directions of movement for a medical instrument, according to one example of principles described herein.

FIG. 2A is a diagram showing possible directions of movement for a medical instrument. According to the present example, a medical instrument (e.g. 26, FIG. 1D) may be aligned with the y-axis 204 illustrated in FIG. 2A. Different motors may be used to move the medical instrument in various directions. For example, a motor may initiate translational movement 212 of the instrument along the x-axis. A motor may initiate translational movement 214 of the instrument along the z-axis. A motor may initiate translational movement 218 of the instrument along the y-axis.

A motor may change the pitch 210 of the instrument. Particularly, the motor may change the rotation angle within the YZ plane. A motor may change the yaw 208 of the instrument. Particularly, the motor may change the rotation angle within the XY plane. And, a motor may rotate 216 the instrument along its axis.

Other motors may move the instrument in an instrument specific manner. For example, an instrument may be a two finger tool such as a gripping tool. A motor may open the grips of the gripping tool or close the grips of the gripping tool. In some cases, some forms of movement, such as the translational movements 212, 214, 218 may be done by moving the manipulator arm (e.g. 51, FIG. 1D). Other movements, such as rotation 216, pitch 210, and yaw 208 may be performed by motors engaged with an instrument carriage associated with the instrument.

Figure 2B:
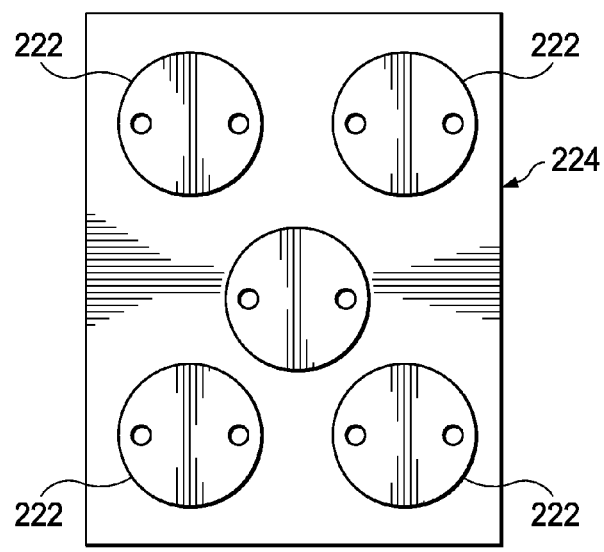
FIG. 2B is a diagram showing an illustrative interface for connecting motors to mechanisms that move a medical instrument, according to one example of principles described herein.

FIG. 2B is a diagram showing an illustrative interface for connecting motors to mechanisms that move a medical instrument. According to the present example, an interface 224 may include 5 disks 222 used to connect motors within a manipulator arm (e.g. 51, FIG. 1D) to a medical instrument (e.g., 26, FIG. 1). Rotation of the motors causes rotation of the disks 222. The disks 222 may be connected to the medical instrument through a system of gears such that a specific rotation of the motor causes a specific degree of movement.

In one example, the interface acts as a sterile instrument interface between the manipulator arm and an instrument carriage. An instrument carriage is a structure that supports a particular medical instrument. The instrument carriage includes a system of gears that will move the instrument in specific directions. The system of gears may be configured to engage with the interface 224. Specifically, the instrument carriage may include disks that correspond with the disks 222 of the interface 224. When engaged, rotation of the disks 222 will cause movement of the system of gears within the instrument carriage, thus causing movement of the instrument within the carriage.

Figure 3:
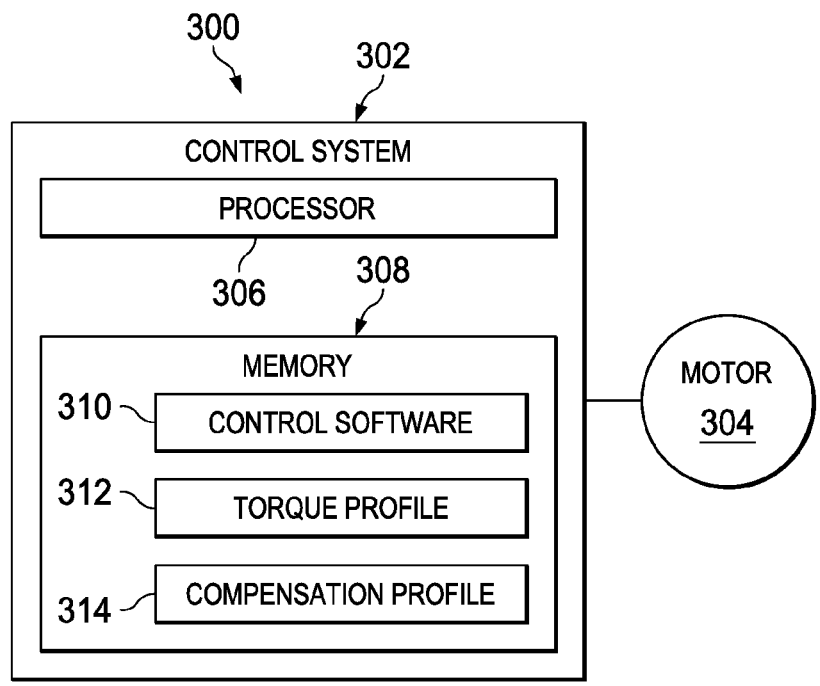
FIG. 3 is a block diagram showing an illustrative control system for a motor, according to one example of principles described herein.

FIG. 3 is a block diagram 300 showing an illustrative control system 302 for a motor 304. Particularly, a control system 302 that may be within the electronics cart (e.g. 18, FIG. 1A) may be used to control motors associated with a manipulator arm (e.g. 51, FIG. 1D) or coupled with gears within an instrument carriage. According to the present example, the control system 302 includes a processor 306 and a memory 308. The memory 308 may store control software 310, a torque profile 312 and a compensation profile 314.

In one example, the control system 302 may be part of the control system 20 as illustrated in FIG. 1A. While only a single motor 304 is illustrated, motor 304 may represent multiple motors 304. Additionally, while only a single torque profile 312 and a single compensation profile 314 are illustrated, torque profile 312 may represent multiple torque profiles 312 and compensation profile 314 may represent multiple compensation profiles 314.

The control system 302 is used to control one or more motors 304. Particularly, the control system 302 may determine that the rotor of a motor 304 should be in a specific position. The control system 302 will then apply the appropriate electrical signal, which will be referred to as the command input signal. The command input signal causes the rotor of the motor 304 to move to the desired position. The control system 302 can also move the motor at a desired speed.

The systems and processes described herein may be applicable to a variety of motors, including, but not limited to AC and DC brushless and brushed motors. In one example, the motor 304 may be a brushless motor with a rotor capable of being placed in a specific angular position. The motor 304 may be assigned to a specific movement of an instrument, such as roll, pitch, or yaw.

The control system 302 includes a processor 306. The processor may actually be several processors 306 acting in concert. The processor 306 executes software (machine readable instructions) that causes the control system 302 to perform desired functions. Such desired functions may include providing the appropriate command input signal to a specific motor to cause specific movement of an instrument.

The memory 308 stores various types of data. Data may be in the form of software. Additionally, data represent other information such as the torque profile 312 or the compensation profile 314. Memory 308 may be either volatile memory or non-volatile memory. Data within volatile memory can be quickly accessed by the processor 306. But data within volatile memory is lost when power is no longer supplied. Non-volatile memory, however, maintains data even when power is not supplied. But, non-volatile memory generally operates much slower than volatile memory.

The control software 310 defines how to control the one or more motors 304 controlled by the control system 302. Specifically, the control system determines how to position the motors based on either inputs from a user or a set of instructions stored in memory 308. For example, an operator of a medical instrument controlled by the motor 304 may use various controls that indicate a specific movement of the medical instrument. The control software 302 includes machine readable instructions that instruct the control system 302 to apply the appropriate signals to the motors 304 that will cause the motors to move in accordance with input from the various controls. In some cases, however, the control software 310 may have a predefined set of signals to apply to the motors 304 to move the motors 304 as desired.

The torque profile 312 defines the torque output of a motor 304 as a function of rotor angle. Specifically, at a steady input current, the torque output is generally not uniform as desired. Particularly, certain rotor angles will have a stronger or weaker torque output. A torque profile may be maintained for each motor 304. The torque profile will be further explained below with the text accompanying FIG. 4A.

The compensation profile 314 defines how an applied electrical signal is adjusted to compensate for torque ripples as indicated by the torque profile. As described above, a torque ripple is a deviation from an ideal torque output in response to a specific input signal. For example, if the motor 304 exhibits a decreased torque output at a specific rotor angle, then the compensation profile 314 can inform the control software 310 to increase the current level when the rotor of the motor is at that specific angle. This may bring the torque output back to the desired level. The compensation profile will be discussed in further detail below with the text accompanying FIG. 4B.

Figure 4A:
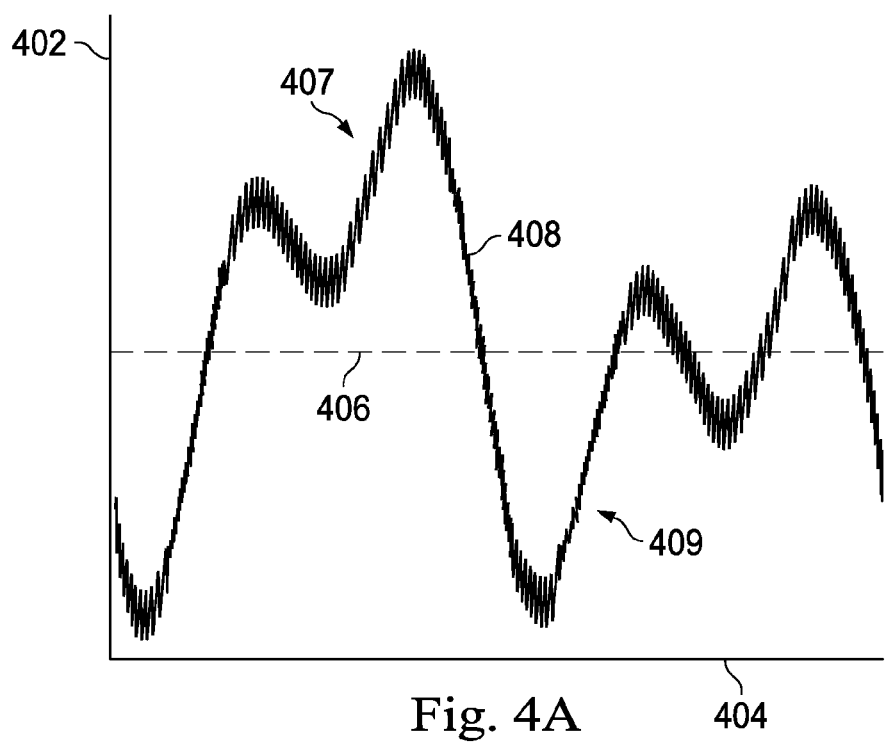
FIG. 4A is a graph showing an illustrative torque profile, according to one example of principles described herein.

FIG. 4A is a graph 400 showing an illustrative torque profile 408. According to the present example, the vertical axis 402 represents torque output. The horizontal axis 404 represents the angular position of a rotor. An ideal torque profile 406 is illustrated by the dotted line. The torque profile 408 does not, however, follow the ideal torque profile 406. The torque profile 408 illustrated in FIG. 4A does not necessarily match an actual torque profile of a real DC brushless motor. Rather, the torque profile 408 is used to illustrate various principles associated with embodiments described herein.

The torque profile 408 represents the torque output at a steady input signal. Thus, when a steady electric current is applied, the torque output changes as the rotor angle changes. As illustrated, the torque profile 408 deviates from the ideal profile 406 at various rotor angles. These deviations 407, 409 are referred to as torque ripples. Torque ripples may cause issues during operation of the motor. For example, when manipulating a medical instrument within a patient, it may be desirable to apply a specific force on the instrument. Variations in motor torque may lead to an undesired force placed on the instrument, potentially harming a patient. Additionally, the torque ripples may cause an inadequate amount of force to be delivered to the medical instrument for the purpose of performing a particular surgical task. Torque ripples may also cause a jittery motion on the instrument, thus complicating the surgical tasks. Therefore, it is desirable to reduce or eliminate the torque ripples.

Torque ripples may be further decomposed into torque harmonics. The torque profile 408 of FIG. 4A represents the combination of a 1× torque harmonic, a 2× torque harmonic, and a 4× torque harmonic. Torque harmonics represent deviations in the torque output at the spatial frequencies that are integer multiples of the inverse of one mechanical revolution of the motor. For example, a 1× torque harmonic may look like a single sine wave across one period of rotor rotation. A 2× torque harmonic may look like two full sine waves across one period of rotor rotation. Using principles described herein, such torque harmonics may be substantially eliminated.

Figure 4B:
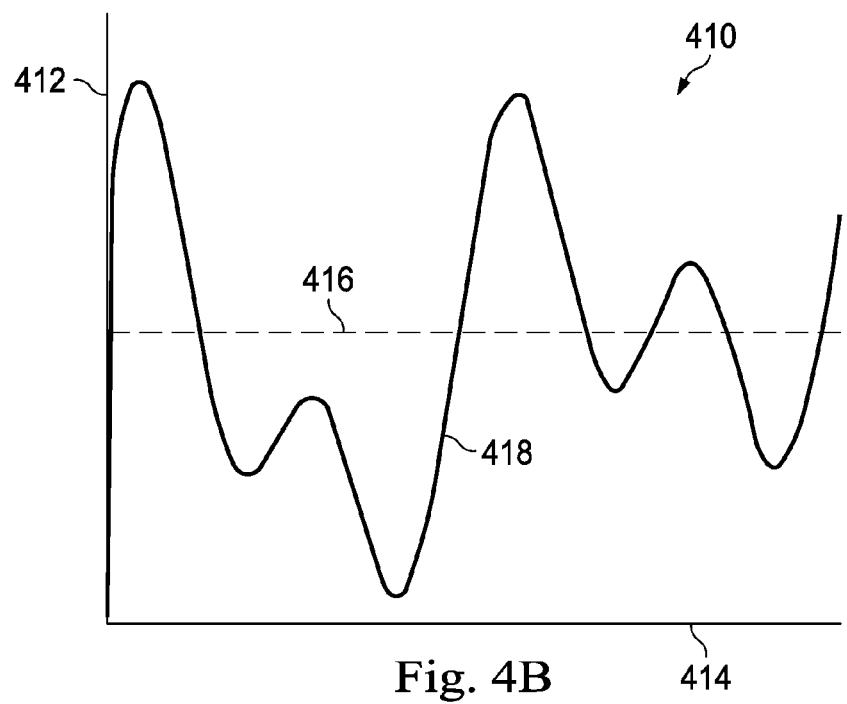
FIG. 4B is a graph showing an illustrative compensation profile, according to one example of principles described herein.

FIG. 4B is a graph 410 showing an illustrative compensation profile 418. According to the present example, the vertical axis 412 represents the compensated command input signal. The horizontal axis 414 represents rotor angle. The dotted line 416 represents a steady input signal. The compensation profile 418 defines the compensated input signal that will produce a substantially uniform torque output.

The compensation profile 418 may be compared to the torque profile 408 of FIG. 4A. Specifically, when the torque profile 408 has a deviation 407 that is more than the ideal torque output 406, the compensation profile 418 defines a smaller input signal. This reduces the torque output, causing it to come closer to the ideal torque output 406. Conversely, when the torque profile 408 has a deviation 409 that is lower than the ideal torque output 406, the compensation profile 418 defines a smaller input signal. This increases the torque output, causing it to come closer to the ideal torque output 406.

In some examples, the compensation may be within a range of 1-2 milliamps. The scale of the compensation profile 418 does not necessarily match with a practical compensation profile used to compensate for the torque profile 408 of FIG. 4A. Rather, the compensation profile 418 of FIG. 4B is used to illustrate principles described herein.

Figure 4C:
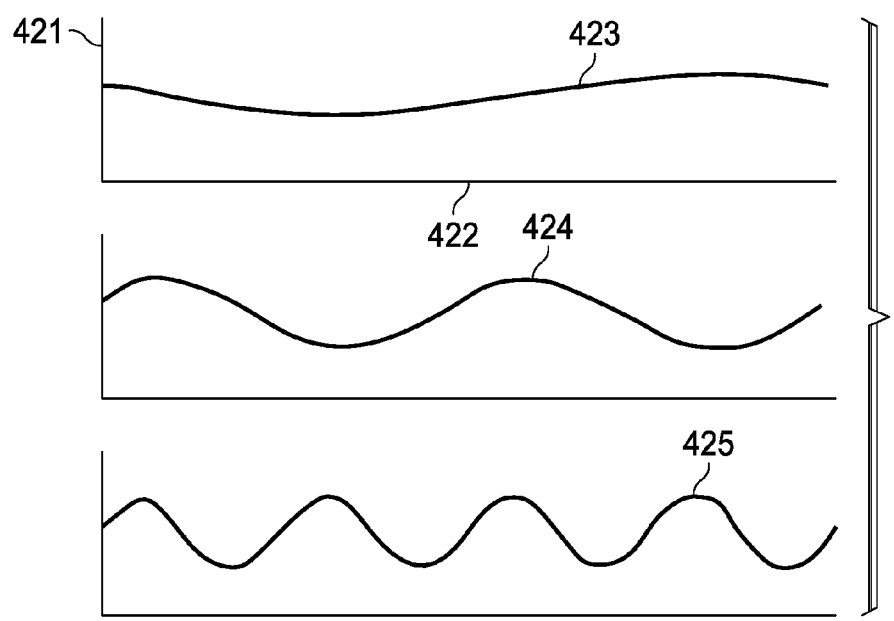
FIG. 4C is a graph showing illustrative harmonic components of a torque profile, according to one example of principles described herein.

FIG. 4C is a graph showing illustrative harmonic components of a torque profile. According to the present example, the vertical axes 421 represent torque output. The horizontal axes 422 represent rotor position. The torque profiles 423, 424, and 425 represent the torque output at 1×, 2×, and 4× harmonics of motor revolution, at a steady input signal.

In some cases, a control system may compensate for torque ripples at specific harmonic components. The first torque profile 423 illustrates a 1× torque harmonic. The second torque profile 424 illustrates a 2× torque harmonic. The third torque profile 425 illustrates a 4× torque harmonic. The sum of these torque harmonics produces a signal similar to the torque profile illustrated in FIG. 4A.

Figure 4D:
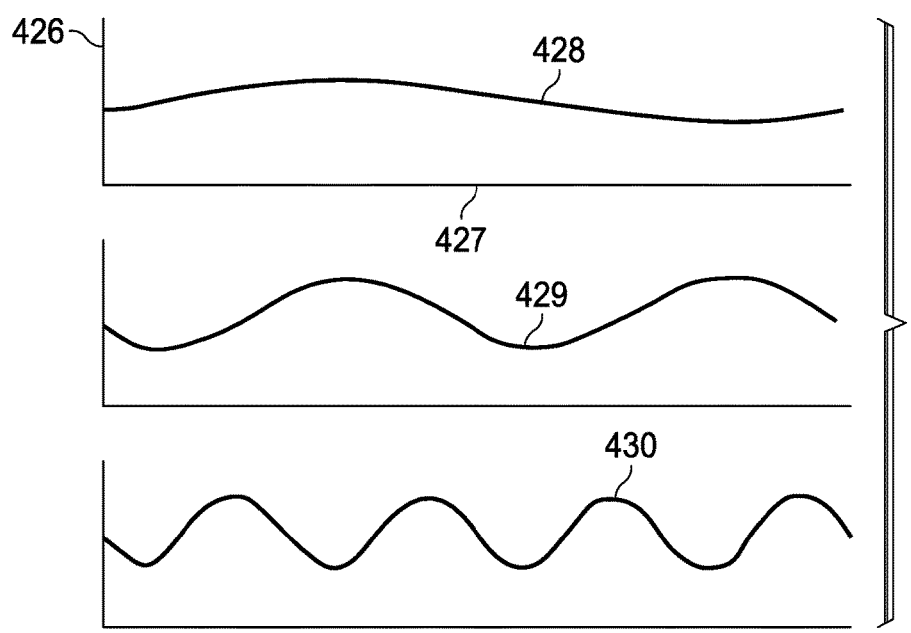
FIG. 4D is a graph showing illustrative harmonic components of a compensation profile, according to one example of principles described herein.

FIG. 4D is a graph showing illustrative harmonic components of a compensation profile. According to the present example, the vertical axes 426 represent a compensated command input signal. The horizontal axes 427 represent rotor position.

The compensation profiles 428, 429, and 430 represent the compensated input signal for torque profiles 423, 424, and 425 respectively. Specifically, the first compensation profile 428 compensates for the 1× torque harmonic. The second compensation profile 429 compensates for the 2× torque harmonic. The third compensation profile 430 compensates for the 4× torque harmonic.

A torque profile for a given motor may change as the load on that motor changes. As described above, the load may be described as the resistance to the torque output. If, for example, the motor is commanded to output a different torque, then the manner of compensating for the torque ripple about that command torque will change. During a surgical operation, the motor may be commanded to produce a variety of different torque outputs as the surgical operation progresses. In some cases, the motor may experience a continuum of different loads during operation.

Figure 5A:
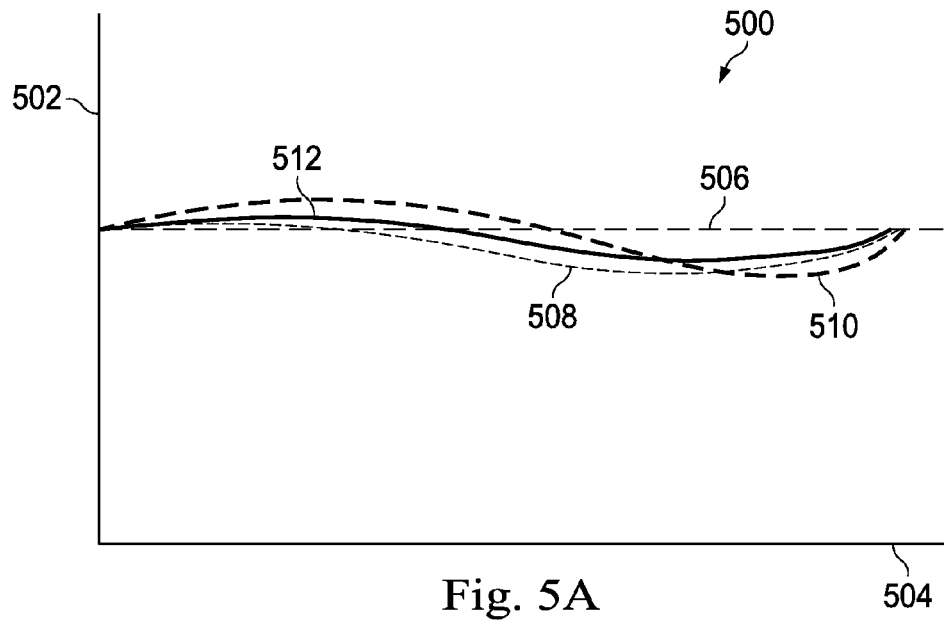
FIG. 5A is a graph showing illustrative torque profiles at different steady-state loads, according to one example of principles described herein.

FIG. 5A is a graph 500 showing illustrative torque profiles at a set of discrete loads. To allow the control system to accurately compensate the torque output at various loads, a set of torque profiles 508, 510, 512 for a given motor may be obtained. Then, a compensation profile for each of those torque profiles 508, 510, 512 may be determined. The compensation profiles may then be interpolated so that the control system can adapt to a given load, regardless of whether a torque profile was obtained for that specific load. The torque profiles 508, 510, 512 illustrated in FIG. 5A do not necessarily match an actual torque profile. Rather, such profiles are used for discussion of principles described herein.

In FIG. 5A, the vertical axis 502 represents torque output and the horizontal axis 504 represents rotor angle. The dotted line 506 represents an ideal torque output. The graph 500 includes a first torque profile 508 at a first load, a second torque profile 510 at a second load, and a third torque profile 512 at a third load. While only three torque profiles are illustrated, a practical implementation of principles described herein may include a larger set of torque profiles.

Figure 5B:
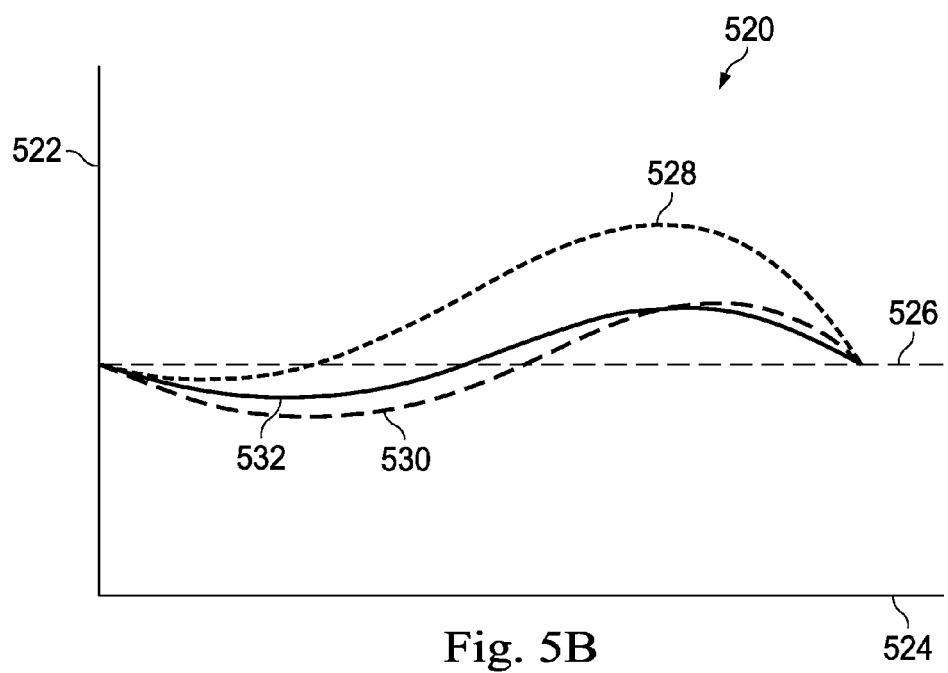
FIG. 5B is a graph showing illustrative compensation profiles for the torque profiles at different steady-state loads, according to one example of principles described herein.

FIG. 5B is a graph 520 showing illustrative compensation profiles for the torque profiles at different loads. According to the present example, the vertical axis 522 represents the input signal, and the horizontal axis 524 represents rotor angle. The dotted line 526 represents a steady input signal.

The first compensation profile 528 corresponds to the first torque profile 508. The second compensation profile 530 corresponds to the second torque profile 510. The third compensation profile 532 corresponds to the third torque profile 512. Similar to the torque profile and compensation profile of FIGS. 4A and 4B, the compensation profiles 528, 530, 532 compensation for deviations from ideal output of the corresponding torque profiles 508, 510, 532.

During operation of the motor, it is likely that a given load experienced by the motor will not match the load of one of the compensation profiles. Thus, the control system can interpolate the compensation profiles to handle the continuum of loads that may be experienced by the motor. For example, during normal operation, the motor may experience a load somewhere between the load of the first torque profile 508 and the load of the second torque profile 510. The control system can then create a compensation profile that is somewhere between the first compensation profile 528 and the second compensation profile 530. In some examples, however, the control system may select the closest compensation profile and use that compensation profile as is.

Each of the obtained torque profiles may be obtained with loads at fixed intervals. The size of these intervals may be selected based on the desired accuracy of the interpolation function. Particularly, a larger set of torque profiles at smaller load intervals may produce a more accurate interpolation function. In contrast, a smaller set of torque profiles at larger load intervals may produce a slightly less accurate interpolation function. But, a smaller set of torque profiles may be more efficient from a computer processing perspective. Particularly, the control system may be able to react more quickly to changing loads.

In some examples, the control system may adjust the input signal in real time based on the torque profile without referring to a specific compensation profile. For example, the control system may refer to the torque profile during operation. If at a specific rotor angle, the torque profile is greater than the ideal torque output, then the control system will reduce the current input. The control system may have logic for determining how much to reduce the current input based on the degree of deviation from the ideal torque output. Specifically, the control system may know that X amount of deviation requires Y amount of input signal adjustment.

For example, a particular motor may be calibrated before operation. During calibration, it is determined how the amplitude of different torque harmonics is affected by varying current input. Specifically, the amplitude of the 1×, 2×, and 4× torque harmonics may be observed to determine how the amplitude varies with current input. For example, it may be determined that for 1 mA of current difference, a change of 9.8 newton meters (Nm) is observed in the 2× harmonic. Thus, a sensitivity profile of 9.8 Nm/mA may be stored by the software of the control system that controls the motor. Then, during normal operation, the control system can use that sensitivity profile to compensate for the 2× harmonic.

In some examples, there may be a different sensitivity profile for each of the harmonics. For example, the sensitivity profile for the 1× harmonic indicates how the amplitude of the 1× harmonic varies with varying current input, the sensitivity profile for the 2× harmonic indicates how the amplitude of the 2× harmonic varies with varying current input, and the sensitivity profile for the 4× harmonic indicates how the amplitude of the 4× harmonic varies with varying current input. Thus, during operation of the motor, each of the different harmonics can be compensated for based on their respective sensitivity profiles. Specifically, the amplitude of the input signal at the respective harmonic can be adjusted appropriately.

Furthermore, during the calibration operation, the different torque harmonics may be measured at different loads. Specifically, the motor is commanded to output a discrete set of loads. Without any compensation, the torque output will vary about the commanded load as illustrated above. For each of the load within the discrete set, the variation in amplitude in response to change in input signal is measured for the different harmonics. A compensation profile for those harmonics can then be stored in the memory of the control system.

During operation of the motor, if the commanded torque matches, or is close to, one of the loads within the discrete set, then the compensation profile for that load may be used to compensate for the various harmonics at that load. In some cases, however, the commanded torque may not match one of the loads within the discrete set. Thus, an interpolation function may be used to determine the appropriate compensation of the input signal for the commanded torque. During a surgical operation, as the commanded torque varies as desired, then the compensation can adjust accordingly based on the compensation profiles of the discrete loads for the various harmonics.

Figure 6:
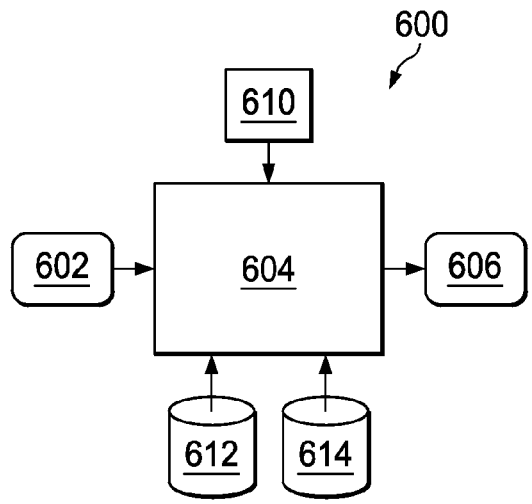
FIG. 6 is a block diagram showing a system for adjusting a command torque to compensate for torque ripples.

FIG. 6 is a block diagram showing a system for adjusting a command torque to compensate for torque ripples. The command torque 602 represents the desired load for the motor. The command torque 602 is fed into the compensation system 604. The compensation system 604 produces an output that will be referred to as the compensated command input signal 606.

The compensation system 604 considers various parameters. Specifically, the compensation system 604 considers the present angular position 610 of the motor as well as the command torque 602. Using these parameters, the compensation system 604 can utilize the compensation profiles 612, 614 to determine how to adjust the command torque 602 at a specific angular position.

In some examples, the compensation profiles 612, 614 may include a load dependent compensation profile 612 and a load independent compensation profile 614. The load dependent compensation profile 612 accounts for torque ripples at various loads. The load independent compensation profile 614 accounts for variations in torque output that are not affected by the load experienced by the motor.

In one example, the compensation system 604 may take into account the command torque 602 and the angular position 610, and determine a multiplier based on information within the load dependent compensation profile 612. This multiplier may then be multiplied by the command torque 602 to produce a first adjustment factor. Additionally, the compensation system 604 may take the present angular position 610 of the motor and determine a second adjustment factor based on information within the load independent compensation profile 614. The compensated command input signal 606 may be a sum of the command torque 602 and both adjustment factors. Either of the adjustment factors may be greater or less than zero, thus allowing the compensated command input signal 606 to be greater or less than the original command torque 602.

Figure 7:
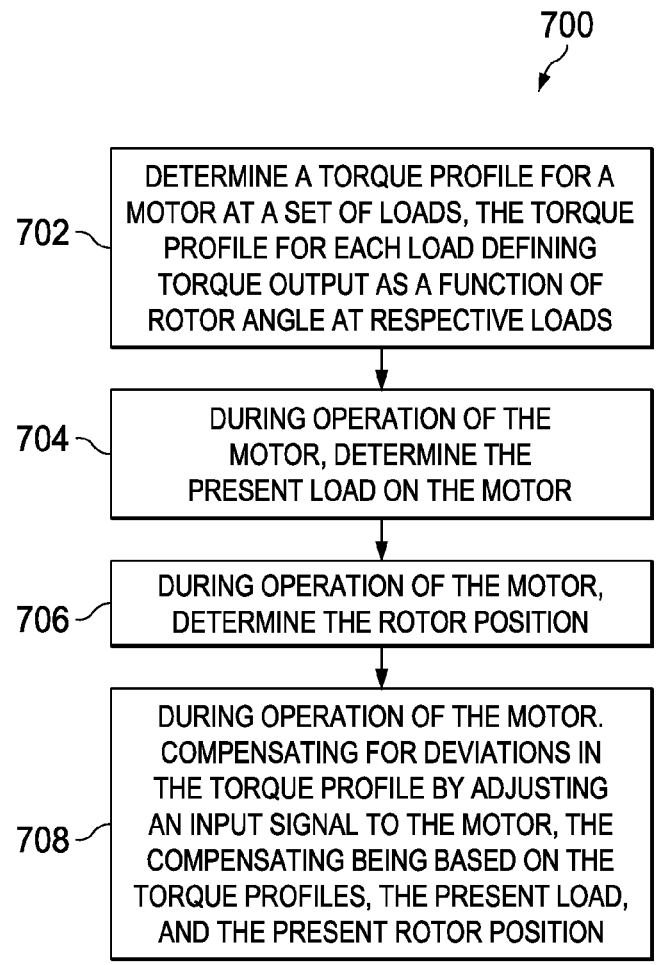
FIG. 7 is a flowchart showing an illustrative method for compensating for torque ripples, according to one example of principles described herein.

FIG. 7 is a flowchart showing an illustrative method 700 for compensating for torque ripples. According to the present example, the method 700 includes a step 702 for determining a torque profile for a motor at a set of loads. The torque profile for each load defining torque output as a function of rotor angle at respective loads. The torque profile may be obtained by applying a steady input signal and measuring the torque output as the rotor angle changes. Due to various reasons, the motor may deviate from an ideal torque output at certain rotor angles, thus causing torque ripples. This may be due to inconsistencies in coil windings of the motors.

According to the present example, the method 700 includes a step 704 for determining the present load on the motor. Various methods may be used to determine the load experienced by the motor. For example, the motor may measure the torque resistance being experienced.

According to the present example, the method 700 includes a step 706 for determining the present rotor position, which is generally provided by some form of rotary position sensors.

According to the present example, the method 700 includes a step 708 for, during operation of the motor, compensating for deviations in the torque profile by adjusting an input signal to the motor, the compensating being based on the torque profiles and an applied load.

Particularly, where the torque profile indicates a decrease in torque output, the compensation profile may indicate an increase in the input signal. Conversely, where the torque profile indicates an increase in torque output, the compensation profile may indicate a decrease in the input signal. Thus, during normal operation, the motor may produce a relatively steady output torque despite the position of the motor. Therefore, whatever device is being moved by the motor can operate more predictably.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method for torque compensation of a motor associated with a medical instrument, the method comprising:

determining, using a control system, a torque profile for the motor, the torque profile defining torque output as a first function of a rotor angle of the motor and of multiple discrete loads;

storing a compensation profile for controlling an input signal to the motor, the compensation profile defining adjustments to the input signal as a second function of the rotor angle of the motor; and applying the compensation profile during operation of the motor.

2. The method of claim 1, further comprising, creating the compensation profile based on the torque profile.

3. The method of claim 1, further comprising, performing a calibration operation on the motor, the calibration operation comprising determining effects on a torque ripple at a harmonic in response to a change in the input signal to the motor.

4. The method of claim 3, further comprising, storing the effects in association with a sensitivity profile for the harmonic.

5. The method of claim 4, wherein compensating for deviations in the torque profile comprises adjusting the input signal based on the sensitivity profile.

6. The method of claim 3, wherein the harmonic is one of: a 1× harmonic, a 2× harmonic, and a 4× harmonic.

7. The method of claim 3, further comprising, storing sensitivity profiles for torque ripples at different harmonics, each of the sensitivity profiles defining variation in amplitudes in response to varying input signals at each of the different harmonics.

8. The method of claim 7, further comprising, during operation of the motor, using each of the sensitivity profiles to compensate for the torque ripples at different harmonics.

9. The method of claim 1, wherein determining the torque profile comprises measuring torque output as a function of the rotor angle with a constant input current.

10. The method of claim 1, wherein the motor comprises a direct current (DC) brushless motor.

11. The method of claim 1, wherein the motor is used to drive a medical instrument attached to a manipulator arm.

12. The method of claim 1, wherein the torque profile identifies torque ripples caused by torque harmonics.

13. A motor system for driving an instrument of a teleoperative system, the motor system comprising:

a motor; and a control system comprising a processor and a memory, the memory comprising machine readable instructions that cause the motor system to:

determine a torque profile for the motor, the torque profile defining torque output as a first function of a rotor angle of the motor and of multiple discrete loads;

store a compensation profile for controlling an input signal to the motor, the compensation profile defining adjustments to the input signal as a second function of the rotor angle of the motor; and apply the compensation profile during operation of the motor.

14. The motor system of claim 13, wherein to determine the torque profile, the control system is configured to measure torque output as a function of the rotor angle with a constant input current.

15. The motor system of claim 13, further comprising, creating the compensation profile based on the torque profile.

16. The motor system of claim 13, wherein the torque profile further defines torque output as a function of an applied load.

17. The motor system of claim 13, wherein determining the compensation profile for a new load comprises interpolating the torque profile for each of the discrete loads.

18. A teleoperative medical device comprising:
a manipulator arm;
a medical instrument detachably connected to the manipulator arm;
a plurality of motors connected to the manipulator arm, each motor of the plurality of motors configured to move the medical instrument in a different manner from another of the plurality of motors;
a control system comprising a processor and a memory, the memory comprising machine readable instructions that when executed by the processor, cause the control system to:
store a separate compensation profile for each motor of the plurality of motors, each compensation profile configured for controlling an input signal to a respective motor, each compensation profile defining adjustments to the input signal of the respective motor as a second function of a rotor angle of the respective motor, each compensation profile being based on a torque profile associated with the respective motor, wherein the torque profile associated with the respective motor defines torque output as a first function of the rotor angle at a set of discrete loads; and
apply each compensation profile during operation of each of the plurality of motors.

19. The teleoperative medical device of claim 18, wherein to apply the compensation profile, the machine readable instructions further cause the control system to interpolate the torque profile at the discrete set of loads to determine the torque profile for each load of the discrete set of loads.

20. The teleoperative medical device of claim 18, wherein each compensation profile comprises a load independent factor that contributes to torque ripples.

* * * * *